United States Patent [19]

Tomcufcik et al.

[11] Patent Number: 4,728,663

[45] Date of Patent: Mar. 1, 1988

[54] N-[(1H-IMIDAZOL-1-YL)ALKYL]BENZ[CD]-INDOL-2-AMINES AND USE IN INHIBITING THROMBOXANE SYNTHETASE ENZYME

[75] Inventors: Andrew S. Tomcufcik, Bergen, N.J.; Walter E. Meyer; Peter S. Chan, Suffern, both of N.Y.; David L. Crandall, Highland Mills, N.Y.

[73] Assignee: American Cyanamid Company, Stamford, Conn.

[21] Appl. No.: 818,315

[22] Filed: Jan. 13, 1986

[51] Int. Cl.[4] .................. C07D 403/12; A61K 31/415
[52] U.S. Cl. .................................... 514/394; 548/336; 548/327; 514/397

[58] Field of Search ................ 548/336, 327; 514/397, 514/394

[56] References Cited

U.S. PATENT DOCUMENTS 4,201,713  5/1980  Harnisch ............................ 548/327

Primary Examiner—Richard A. Schwartz
Assistant Examiner—Robert C. Whittenbaugh
Attorney, Agent, or Firm—R. P. Raymond

[57] ABSTRACT

N-[(1H-imidazol-1-yl)alkyl]benz[cd]-indol-2 amines useful as inhibitors of thromboxane synthetase enzyme, hypotensive agents and cardioprotective agents are described.

23 Claims, No Drawings

N-[(1H-IMIDAZOL-1-YL)ALKYL]BENZ[CD]-INDOL-2-AMINES AND USE IN INHIBITING THROMBOXANE SYNTHETASE ENZYME

SUMMARY OF THE INVENTION

This invention relates to new organic compounds and, more particularly, is concerned with novel substituted and unsubstituted N-[(1H-imidazol-1-yl)alkyl]-benz[cd]indol-2-amines which may be represented by the following structural formula:

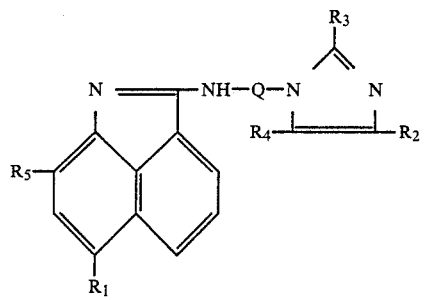

wherein $R_1$ is selected from the group consisting of hydrogen, bromo, chloro and dimethylaminosulfonamide; $R_2$ is selected from the group consisting of hydrogen and alkyl($C_1$–$C_3$); $R_3$ is selected from the group consisting of hydrogen, alkyl($C_1$–$C_3$) and phenyl; $R_4$ is hydrogen or when taken together with $R_2$ is —CH=CH—CH=CH—; $R_5$ is selected from the group consisting of hydrogen and chloro; and Q is selected from the group consisting of —$(CH_2)_n$—, where n is an integer 2–12,

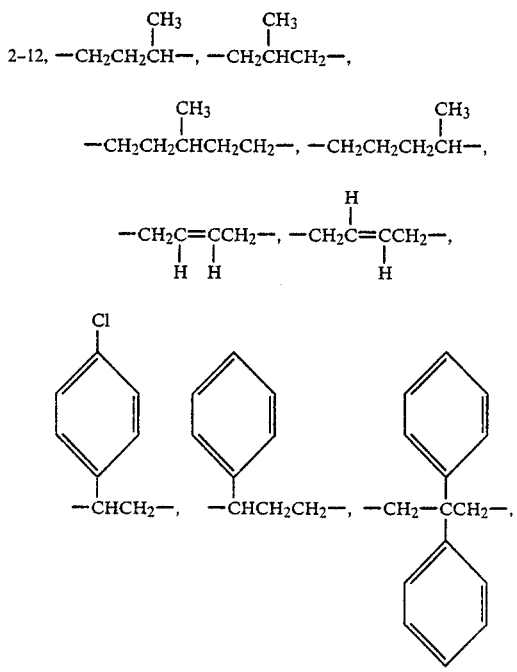

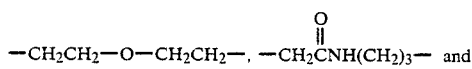

and the pharmacologically acceptable salts thereof.

The organic bases of this invention form non-toxic acid-addition salts with a variety of pharmacologically acceptable organic and inorganic salt-forming reagents. Thus acid-addition salts, formed by admixture of the organic free base with one or more equivalents of an acid, suitably in a neutral solvent, are formed with such acids as sulfuric, phosphoric, hydrochloric, hydrobromic, hydroiodic, sulfamic, citric, lactic, malic, succinic, maleic, fumaric, tartaric, acetic, benzoic, gluconic, ascorbic and the like. For the purpose of this invention the free bases are equivalent to their non-toxic acid-addition salts.

DETAILED DESCRIPTION OF THE INVENTION

The compounds of the present invention may be readily prepared according to the following reaction scheme, wherein $R_1$, $R_2$, $R_3$, $R_4$, $R_5$ and Q are as described hereinabove.

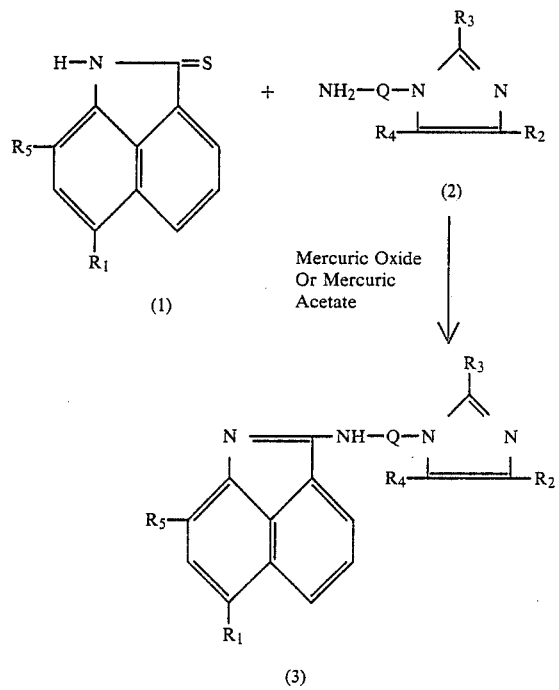

In accordance with the above reaction scheme a substituted benz[cd]indole-2-thiol (1) is reacted with a substituted 1H-imidazole-1-alkanamine (2) and mercuric oxide or mercuric acetate in a suitable solvent such as ethanol or methylcellosolve at reflux temperature for several hours giving the desired compounds.

Alternatively a substituted 2-(methylthio)benz[cd]indole of the formula:

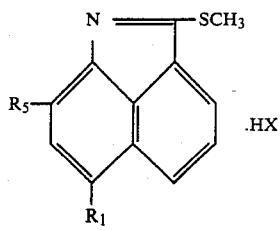

may be used instead of the benz[cd]indole-2-thiol; this reaction is carried out in the absence of the mercuric compounds.

The compounds of this invention inhibit thromboxane synthetase enzyme. Thus, these compounds are useful in the treatment of diseases characterized by an imbalance of thromboxane A₂/prostacyclin such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elsevier/North-Holland Biomedical Press, pp 137-150 (1981)]. Prostacyclin (PGI$_2$) is a potent vasodilator and platelet aggregation inhibitor, whereas thromboxane (TXA$_2$) is a powerful vasoconstrictor and causative of platelet aggregation. TXA$_2$ is synthesized by thromboxane synthetase enzyme located in, for example, blood platelets. When TXA$_2$ production is increased relative to PGI$_2$, platelet aggregation, thrombosis and vasopasm may occur [Lancet (i), 1216 (1977); Lancet, 479 (1977); *Science*, 1135 (1976); *Amer. J. Cardiology*, 41 787 (1978)]. TXA$_2$ synthetase inhibitors have been shown to have superior anti-thrombotic action to that of aspirin [*J. Clin. Invest.*, 65 400 (1980); *Br. J. Pharmac.*, 76, 3 (1982)].

The role of prostaglandins including TXA$_2$ and PGI$_2$ in ischemic heart patients has been reviewed [*Cardiovascular Pharmacology of the Prostaglandins*, A. G. Herman, P. M. Vanhoute, H. Denolin and A. Goosens, eds., Raven Press, New York, pp 361-374 (1982)]. Injection of TXA$_2$ into coronary arteries of guinea pigs and rabbits causes myocardial ischemia and subendocardial necrosis [*Drugs of the Future*, 7, 331 (1982); *Proc. Jap. Acad.*, 53(B), 38 (1977); *Eur. J. Pharmacol.*, 53 49(1978)]. Recent research has demonstrated the beneficial effects of PGI$_2$ and selective inhibition of thromboxane synthetase on ischemic myocardium in canines [*J. Cardiovascular Pharmacology*, 4, 129 (1982)]. Thus compounds which selectively inhibit thromboxane synthetase (and hebnce TXA$_2$) without adversely affecting PGI$_2$ are useful in the treatment of vascular diseases such as ischemia and migraine. In addition, inhibition of TXA$_2$ formation may effectively treat platelet aggregation and prevent thrombosis.

Under urethan anesthesia, 10 μl of arterial blood from Okamoto-Aoki spontaneously hypertensive rats (SHR) (Taconic Farms, Germantown, N.Y.) between 19 and 24 weeks in age was collected in one ml of 3.2% sodium citrate in a polystyrene tube. The blood was diluted with 3 ml of cold saline and centrifuged at room temperature for 15 minutes at 460 xg. The platelet rich plasma (PRP) was separated. The platelets were isolated by centrifuging the PRP for 10 minutes at 1060 xg and were washed in 4 ml of cold oxygenated Krebs phosphate buffer, pH 7.4. The chilled platelets, recovered from centrifuging at 800 xg for 10 minutes, were resuspended in oxygenated Krebs phosphate buffer and diluted to contain 4.5–6.0×10⁴ platelets/μl.

The inhibition of thromboxane (TX) formation was studied by determing the concentration of thromboxane B$_2$ (TXB$_2$), the stable hydrolysis product of TXA$_2$. Assay samples, prepared on ice, contained 200 μl platelet suspension, 50 μl saline, and 50 μl vehicle or drug under study. The samples were incubated for 10 minutes at 37° C. in a metabolic shaker. The reaction was terminated by immersing the tubes in an ice bath and adding 50 μl of 0.5M citric acid. The samples were centrifuged for 10 minutes in a refrigerated centrifuge and the supernatants thus obtained were decanted and stored at −20° C. The TXB$_2$ content for each sample was determined by a direct radioimmunoassay (RIA) utilizing a TXB$_2$ specific RIA kit purchased from New England Nuclear, Boston, Mass. and expressed as pg TXB$_2$ formed minute$^{-1}$ sample $^{-1}$, from which the percent inhibition of TXB$_2$ formation was calculated. The results of this test on representative compounds of this invention appear in Table I below.

TABLE I

| Thromboxane Synthetase Enzyme Inhibition | | |
|---|---|---|
| Compound | Dose | % Inhibition |
| N—[3-(1H—Imidazol-1-yl)propyl]benz[cd]indol-2-amine, dihydrochloride | 10⁻⁴ | 85 |
| 6-Bromo-N—[3-(1H—imidazol-1-yl)propyl]benz[cd]indol-2-amine, dihydrochloride | 10⁻⁴ | 85 |
| N—[3-(1H—Imidazol-1-yl)butyl]benz[cd]indol-2-amine, dihydrochloride | 10⁻⁴ | 92 |
| N—[1-(4-Chlorophenyl)-2-(1H—imidazol-1-yl)ethyl]benz[cd]indol-2-amine, fumarate | 10⁻⁴ | 35 |
| N—[3-(1H—Imidazol-1-yl)-2-methylpropyl]benz[cd]indol-2-amine, dihydrochloride | 10⁻⁴ | 95 |
| N—[3-(1H—Imidazol-1-yl)-1-phenylpropyl]benz[cd]indol-2-amine, fumarate | 10⁻⁴ | 100 |
| N—[3-(1H—Imidazol-1-yl)-2-methylpropyl]benz[cd]indol-2-amine, fumarate | 10⁻⁴ | 100 |
| N—[5-(1H—Imidazol-1-yl)pentyl]benz[cd]indol-2-amine, fumarate | 10⁻⁴ | 95 |
| (Z)—N—[4-(1H—Imidazol-1-yl)-2-butenyl]benz[cd]indol-2-amine, dihydrochloride | 10⁻⁴ | 97 |
| N—[3-(2-Phenyl-1H—imidazol-1-yl)propyl]benz[cd]indol-2-amine, hydroiodide | 10⁻⁴ | 100 |
| N—[3-(2-Methyl-1H—imidazol-1-yl)propyl]benz[cd]indol-2-amine, hydroiodide | 10⁻⁴ | 82 |
| N—[4-(1H—Imidazol-1-yl)butyl]benz[cd]indol-2-amine, hydroiodide | 10⁻⁴ | 100 |
| (Z)—N—[4-(1H—Imidazol-1-yl)-2-butenyl]benz[cd]indol-2-amine, hydroiodide | 10⁻⁴ | 100 |
| (E)—N—[4-(1H—Imidazol-1-yi)-2-butenyl]benz[cd]indol-2-amine, hydroiodide | 10⁻⁴ | 100 |
| N—[3-(1H—Benzimidazol-1-yl)propyl]benz[cd]indol-2-amine, fumarate | 10⁻⁴ | 90 |
| N—[3-(1H—Benzimidazol-1-yl)propyl]benz[cd]indol-2-amine | 10⁻⁴ | 60 |
| N—[4-(1H—Imidazol-1-yl)butyl]benz[cd]indol-2-amine, fumarate | 10⁻⁴ | 100 |
| N—[5-(1H—Imidazol-1-yl)-3-methylpentyl]benz[cd]indol-2-amine, dihydrochloride | 10⁻⁴ | 100 |
| N—[10-(1H—Imidazol-1-yl)decyl]benz[cd]indol-2-amine, fumarate | 10⁻⁴ | 65 |
| N—[2-(1H—imidazol-1-yl)ethyl]benz[cd]indol-2-amine | 10⁻⁴ | 71 |
| 6-Bromo-N—[3-(1H—imidazol-1-yl)butyl]benz[cd]indol-2-amine | 10⁻⁴ | 100 |
| N,N—Dimethyl-2-[[3-(1H—imidazol-1-yl)butyl]amino]benz[cd]indol-6-sulfon- | 10⁻⁴ | 99 |

TABLE I-continued

| Thromboxane Synthetase Enzyme Inhibition | | |
|---|---|---|
| Compound | Dose | % Inhibition |
| N,N—Dimethyl-2-[[3-(1H—imidazol-1-yl)-propyl]amino]benz[cd]indol-6-sulfonamide | $10^{-4}$ | 100 |
| 6-Bromo-N—[10-(1H—Imidazol-1-yl)-decyl]benz[cd]indol-2-amine | $10^{-4}$ | 94 |
| 6-Bromo-N—[4-(1H—imidazol-1-yl)-butyl]benz[cd]indol-2-amine | $10^{-4}$ | 98 |
| 2-(Benz[cd]indol-2-ylamino)N—[3-(1H—imidazol-1-yl)propyl]acetamide | $10^{-4}$ | 100 |
| N—[[4-(1H—Imidazol-1-ylmethyl)phenyl]-methyl]benz[cd]indol-2-amine, fumarate | $10^{-4}$ | 100 |
| 6,8-Dichloro-N—[10-(1H—imidazol-1-yl)-decyl]benz[cd]indol-2-amine | $10^{-4}$ | 96 |
| 6,8-Dichloro-N—[3-(1H—imidazol-1-yl)-propyl]benz[cd]indol-2-amine | $10^{-4}$ | 97 |
| 6-Bromo-N—[5-(1H—imidazol-1-yl)-pentyl]benz[cd]indol-2-amine | $10^{-5}$ | 97 |
| 6,8-Dichloro-N—[5-(1H—imidazol-1-yl)-pentyl]benz[cd]indol-2-amine | $10^{-5}$ | 100 |
| 6-Chloro-N—[5-(1H—imidazol-1-yl)-pentyl]benz[cd]indol-2-amine | $10^{-5}$ | 100 |
| N—[4-(1H—Imidazol-1-yl)pentyl]benz[cd]indol-2-amine, fumarate | $10^{-5}$ | 99 |
| 6-Chloro-N—[4-(1H—imidazol-1-yl)-butyl]benz[cd]indol-2-amine, fumarate | $10^{-5}$ | 100 |

The novel compounds of the present invention have been found to be highly useful for inhibiting thromboxane synthetase in mammals when administered in amounts ranging from about 1.0 mg to about 20.0 mg/kg of body weight per day. A preferred dosage regimen for optimum results would be from about 1.0 mg to about 10.0 mg/kg of body weight per day. Such dosage units are employed that a total of from about 70 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

HYPOTENSIVE ACTIVITY IN SPONTANEOUSLY HYPERTENSIVE RATS

The novel compounds of the present invention are active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y., having an average mean arterial blood pressure of $160 \pm 1.5$ mm of mercury, were used in the test. One to 3 rats were used per test compound. A rat was dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading was given 24 hours later. At 28 hours after the initial dose the mean arterial blood pressure (MABP) was measured. The procedure was repeated in a second and third rat when necessary.

The results of this test on representative compounds of the present invention appear below in Table II.

TABLE II

| Hypotensive Activity | |
|---|---|
| Compound | Avg. MABP in mm Hg (No. of Rats) |
| N—[3-(1H—Imidazol-1-yl)propyl]benz[cd]-indol-2-amine, dihydrochloride | 87 (2) |
| 6-Bromo-N—[3-(1H—imidazol-1-yl)propyl]-benz[cd]indol-2-amine, dihydrochloride | 117 (2) |
| N—[3-(1H—Imidazol-1-yl)butyl]benz[cd]-indol-2-amine, dihydrochloride | 104 (2) |
| N—[3-(4-Methyl-1H—imidazol-1-yl)propyl]-benz[cd]indol-2-amine, dihydrochloride | 106 (2) |
| N—[3-(1H—Imidazol-1-yl)propyl]benz[cd]-indol-2-amine, dihydrochloride | 113 (2) |
| N—[5-(1H—imidazol-1-yl)pentyl]benz[cd]-indol-2-amine, fumarate | 111 (2) |
| (Z)—N—[4-(1H—Imidazol-1-yl)-2-butenyl]-benz[cd]indol-2-amine, dihydrochloride | 77 (2) |
| N—[3-(1H—Imidazol-1-yl)-2,2-diphenyl-propyl]benz[cd]indol-2-amine | 127 (3) |
| (Z)—N—[4-(1H—Imidazol-1-yl)-2-butenyl]-benz[cd]indol-2-amine, fumarate | 102 (1) |
| N—[4-(1H—Imidazol-1-yl)butyl]benz[cd]-indol-2-amine, hydroiodide | 74 (2) |
| (Z)—N—[4-(1H—Imidazol-1-yl)-2-butenyl]-benz[cd]indol-2-amine, hydroiodide | 106 (2) |
| N—[3-(1H—Benzimidazol-1-yl)propyl]benz-[cd]indol-2-amine, fumarate | 123 (3) |
| N—[3-(1H—Benzimidazol-1-yl)propyl]benz-[cd]indol-2-amine | 124 (3) |
| N—[4-(1H—Imidazol-1-yl)butyl]benz[cd]-indol-2-amine, fumarate | 106 (2) |
| N—[5-(1H—Imidazol-1-yl)-3-methylpentyl]-benz[cd]indol-2-amine, dihydrochloride | 92 (2) |
| N—[10-(1H—Imidazol-1-yl)decyl]benz[cd]-indol-2-amine, fumarate | 124 (3) |
| N—[10-(1H—Imidazol-1-yl)decyl]benz[cd]-indol-2-amine, dihydrochloride | 124 (3) |
| N—[2-(1H—Imidazol-1-yl)ethyl]benz[cd]-indol-2-amine | 100 (2) |
| N—[2-[2-(1H—Imidazol-1-yl)ethoxy]ethyl]-benz[cd]indol-2-amine, fumarate | 108 (2) |
| N—[8-(1H—Imidazol-1-yl)octyl]benz[cd]-indol-2-amine, dihydrochloride | 111 (2) |
| N—[2-(1H—Imidazol-1-yl)ethyl]benz[cd]-indol-2-amine, fumarate | 97 (2) |
| 6-Bromo-N—[3-(1H—Imidazol-1-yl)butyl]-benz[cd]indol-2-amine | 120 (2) |
| 6-Bromo-N—[4-(1H—Imidazol-1-yl)butyl]-benz[cd]indol-2-amine | 120 (2) |
| N—[[4-(1H—Imidazol-1-ylmethyl)phenyl]-methyl]benz[cd]indol-2-amine, fumarate | 121 (3) |
| 6,8-Dichloro-N—[10-(1H—imidazol-1-yl)-decyl]benz[cd]indol-2-amine | 121 (2) |
| 6,8-Dichloro-N—[3-(1H—imidazol-1-yl)-butyl]benz[cd]indol-2-amine | 102 (2) |
| 6,8-Dichloro-N—[3-(1H—imidazol-1-yl)-propyl]benz[cd]indol-2-amine | 102 (2) |
| 6,8-Dichloro-N—[4-(1H—imidazol-1-yl)-butyl]benz[cd]indol-2-amine | 115 (2) |
| 6-Bromo-N—[5-(1H—imidazol-1-yl)pentyl]-benz[cd]indol-2-amine | 118 (3) |
| 6,8-Dichloro-N—[5-(1H—imidazol-1-yl)-pentyl]benz[cd]indol-2-amine | 119 (2) |
| N—[4-(1H—imidazol-1-yl)pentyl]benz[cd]-indol-2-amine, fumarate | 97 (2) |
| 6-Chloro-N—[4-(1H—imidazol-1-yl)butyl]-benz[cd]indol-2-amine, fumarate | 115 (2) |
| 6-Chloro-N—[3-(1H—imidazol-1-yl)propyl]-benz[cd]indol-2-amine | 124 (4) |

The compounds of this invention are also considered to be cardio-protective in that they are anti-arrhythmic agents as established in the following test.

THEVETIN (CARDIAC GLYCOSIDE)-INDUCED ARRHYTHMIA IN GUINEA PIGS

Male guinea pigs, weighing 300-500 g each, from Summit View Farms, Belvidere, N.J., were anesthetized by intraperitoneal administration of urethan at 1500 mg/kg. The animals were then restrained in a supine position. Electrocardiogram leads were attached to the four limbs and Lead II of the electrocardiogram was monitored.

The neck region was exposed and the jugular vein was cannulated. The test compounds were dissolved in saline and administered intravenously at the indicated doses, via a cannula which was then flushed with saline. Five minutes after the test compound was administered, thevetin dissolved in saline was administered by infusion through a cannula at a dose of 0.1 mg/kg/minute in a volume of 0.1 ml. The time until the P wave of the electrocardiogram disappeared was determined.

Based on the data obtained from 126 guinea pigs treated with physiological saline, but no test compound, the time it took for thevetin infusion to cause P wave disappearance on the electrocardiogram or the appearance of irregular heart beat (ectopic heart beat, etc.) was 22.91±0.5 minutes (means ±S.E.M).

A compound that protects guinea pigs for 31 minutes before arrhythmia occurred is considered active.

Propanolol at an intravenous dose of 2 mg/kg protected the guinea pigs for 47.0±4.1 minutes before arrhythmia occurred and was active in this test.

4-[2-(1H-Imidazol-1-yl)ethoxy]benzoic acid, monohydrochloride (Dazoxiben hydrochloride, Pfizer, Inc.) and 2-methyl-3-[4-(3-pyridinylmethyl)phenyl]-2-propenoic acid, sodium salt (OKY-1581, Ono Pharm.), both literature-described thromboxane synthetase inhibitors, at intravenous doses as high as 20 mg/kg were inactive (22.2±1.9 and 24.3±2.2 minutes, respectively).

The results of this test on typical compounds of this invention appear in Table III.

TABLE III

| Compound | No. of Guinea Pigs | IV Dose (mg/kg) | Time (Minutes) Before Induced Arrhythmia |
|---|---|---|---|
| N—[3-(1H—Imidazol-l-yl)propyl]-benz[cd]indol-2-amine, dihydrochloride | 4 | 10 | 48.5 |
| N—[3-(1H—Imidazol-l-yl)-2-methylpropyl]benz[cd]indol-2-amine, fumarate | 4 | 20 | 34.5 |
| N—[3-(1H—Imidazol-l-yl)-2,2-diphenylbenz[cd]indol-2-amine | 4 | 10 | 41 |
| N—[4-(1H—Imidazol-1-yl)butyl]-benz[cd]indol-2-amine, fumarate | 25 | 10 | 31 |
| N—[10-(1H—Imidazol-l-yl)decyl]-benz[cd]indol-2-amine, fumarate | 6 | 10 | 34.2 |
| 6-Bromo-(N—[3-(1H—imidazol-l-yl)butyl]benz[cd]indol-2-amine | 3 | 30 | 34.7 |
| 6,8-Dichloro-(N—[3-(1H—imidazol-1-yl)butyl]benz[cd]indol-2-amine | 6 | 20 | 32 |
| 6,8-Dichloro-(N—[5-(1H—imidazol-1-yl)pentyl]benz[cd]indol-2-amine | 5 | 20 | 33.4 |
| 6-Chloro-(N—4-(1H—imidazol-1-yl)butyl]benz[cd]indol-2-amine, fumarate | 2 | 10 | 31.5 |
| 6-Bromo-(N—[5-(1H—imidazol-l-yl)pentyl]benz[cd]indol-2-amine | 2 | 20 | 37 |
| 2-[[3-(1H—Imidazol-1-yl)butyl]-amino]-(N,N—dimethylbenz[cd]-indole-6-sulfonamide | 9 | 10 | 33.6 |
| N—[3-(1H—Imidazol-l-yl)phenylpropyl]benz[cd]indol-2-amine, fumarate | 8 | 30 | 34 |
| (E)-(N—[4-(1H—Imidazol-l-yl)-2-butenyl]benz[cd]indol-2-amine, monohydroiodide | 3 | 10 | 34.3 |
| 2-[[3-(1H—Imidazol-l-yl)-propyl]amino]-(N,N'—dimethyl-benz[cd]indole-6-sulfonamide | 5 | 20 | 33.4 |
| 2-(Benz[cd]indol-2-ylamino)-N—[3-(1H)—imidazol-l-yl)lpropyl]-acetamide | 2 | 25 | 33 |

It is known that drugs that have α-adrenoceptor binding activity are capable of blocking α-adrenoceptors on the heart muscle and are thus implicated in the prevention of several injuries that are associated with myocardial infraction.

IN VITRO FOR α-ADRENOCEPTOR BINDING IN HEART MEMBRANE

Mycardial membrane protein was isolated from Sprague-Dawley rats by an art recognized method. Each test compound was then incubated at a concentration of 10 μM, in the presence of a known amount of membrane (about 500 μg) and a radioactive ligand, $3_H$-prazocin. Displacement of the ligand by the test compound was then calculated by assessing the amount of radioactivity associated with membrane using a liquid scintillation counter. Specific binding of 65% or more of the total radioactivity to the membrane in the presence of the test compound is the criterion for designating a particular compound as "in vitro active". The results of this test appear in the following Table.

| In Vitro Results for α-Adrenoceptor Binding in Heart Membrane | |
|---|---|
| Compound | Percent* Specific Binding |
| N—[3-(2-Methyl-1H—imidazol-1-yl)propyl]benz[cd]-indol-2-amine, monohydroiodide | 66.7 |
| N—[4-(1H—Imidazol-1-yl)butyl]benz[cd]indol-2-amine, fumarate | 78.4 |
| N—[10-(1H—Imidazol-1-yl)decyl]benz[cd]indol-2-amine, fumarate | 64.8 |
| N—[10-(1H—Imidazol-1-yl)decyl]benz[cd]indol-2-amine, dihydrochloride | 87.1 |
| N—[4-(1H—Imidazol-1-yl)pentyl]benz[cd]indol-2-amine, fumarate | 65.3 |
| 6-Chloro-N—[4-(1H—imidazol-1-yl)butyl]benz[cd]-indol-2-amine, fumarate | 65.6 |
| N—[3-(1H—Imidazol-1-yl)propyl]benz[cd]indol-2-amine, difumarate | 71.7 |

*Mean of three separate incubations containing test compound at 10 μM and 2.5 nM of $^3H$—prazocin.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The perservatives which may be used for these purposes are, for example, myristyl-gamma-picolinium chloride, benzalkonium chloride, phenethyl alcohol, p-chlorophenyl-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

N-[3-(1H-Imidazol-1-yl)propyl]benz[cd]indol-2-amine, dihydrochloride

A mixture of 6.2 g of benz[cd]indole-2-thiol and 4.4 g of 3-(1H-imidazol-1-yl)propanamine in 250 ml of ethanol was stirred and heated. An 8.0 g portion of mercuric oxide was added, the mixture was stirred at reflux for 20 hours, then filtered and the insolubles washed with 100 ml of hot ethanol. The combined filtrate and wash was taken to dryness in vacuo. The residual oil was dissolved in a mixture of 100 ml of water and 15 ml of concentrated hydrochloric acid, treated with activated charcoal and then filtered. The filtrate was taken to dryness in vacuo. The residual oil was mixed with 150 ml of ethanol and taken to dryness in vacuo. This residue was dissolved in 100 ml of boiling ethanol, then filtered and the filtrate cooled at −10° C. This filtrate was then reheated to boiling, 300 ml of acetone were added, the mixture treated with activated charcoal and then filtered. The filtrate was cooled at −10° C. and the resulting precipitate collected, washed with acetone and dried in vacuo at 60° C., giving 3.4 g of the desired product, mp 262°–265° C. (dec.).

EXAMPLE 2

6-Bromo-N-[3-(1H-imidazol-1-yl)propyl]benz[cd]indol-2-amine, dihydrochloride

A mixture of 4.0 g of 6-bromo-2-benz[cd]indole-2-thiol and 2.0 g of 3-(1H-imidazol-1-yl)propanamine in 125 ml of 2-methoxyethanol was stirred and heated. A 3.8 g portion of mercuric oxide was added and the mixture was stirred at reflux for 7 hours, then clarified while hot. The filtrate was cooled to −10° C., acidified with 5 ml of concentrated hydrochloric acid and then taken to dryness in vacuo. The residue was dissolved in 150 ml of boiling ethanol, filtered, cooled to −10° C. and 150 ml of acetone added. This mixture was allowed to stand at 10° C., then the precipitate was collected, washed with acetone and dried in vacuo at 60° C., giving 1.5 g of the desired product, mp 281°–283° C. (dec.).

EXAMPLE 3

N-[3-(1H-Imidazol-1-yl)butyl]benz[cd]indol-2-amine, dihydrochloride

A mixture of 2.8 g of 3-(1H-imidazol-1-yl)butanamine, 6.5 g of 2-(methylthio)benz[cd]indole hydroiodide and 250 ml of ethanol was stirred at reflux for 16 hours, then 2 g of potassium carbonate and 10 ml of water were added and the mixture was taken to dryness in vacuo. The residue was partitioned between 250 ml of dichloromethane and 100 ml of water. The dichloromethane layer was separated, dried over magnesium sulfate, filtered and the filtrate taken to dryness in vacuo. The residue was mixed with 200 ml of 2-methoxyethanol and 5 ml of concentrated hydrochloric acid, then taken to dryness in vacuo. The residue was dissolved in 50 ml of hot ethanol, diluted with 200 ml of acetone, cooled to −10° C., diluted with 200 ml of ether and then filtered. The filtrate was diluted with 400 ml of ether and cooled at −10° C. The precipitate was collected, washed with ether and dried in vacuo at 60° C., giving 0.8 g of the desired product, mp 145–150 (dec.).

EXAMPLE 4

N-[1-(4-Chlorophenyl)-2-(1H-imidazol-1-yl)ethyl]-benz[cd]indol-2-amine, fumarate A mixture of 2 g of 1-(4-chlorophenyl)-2-(1H-imidazol-1-yl)ethanamine, 2.95 g of 2-(methylthio)benz[cd]indole hydroiodide and 200 ml of ethanol was reacted as described in Example 3. The resulting base was dissolved in 50 ml of acetone, filtered and the filtrate added to a solution of 0.3 of fumaric acid in 50 ml of acetone. The mixture was cooled to −10° C., the solid collected, washed with acetone and ether and dried at 60° C. in vacuo, giving 0.6 g of the desired product, mp 130°–135° C. (dec.).

EXAMPLE 5

N-[3-(4-Methyl-1H-imidazol-1-yl)propyl[benz[cd]indol-2-amine, dihydrochloride

A 1.4 g portion of 3-(4-methyl-1H-imidazol-1-yl)propanamine, 1.9 g of benz[cd]indol-2-thiol, 250 ml of ethanol and 2.5 g of mercuric oxide were reacted as described in Example 1, giving 0.3 g of the desired product, mp 250°–255° C. (dec.).

EXAMPLE 6

N-[3-(1H-Imidazol-1-yl)-2-methylpropyl]benz[cd]indol-2-amine, dihydrochloride

A mixture of 7 g of 2-methyl-3-(1H-imidazol-1-yl)propanamine, 9.3 g of benz[cd]indol-2-thiol, 300 ml of ethanol and 13 g of mercuric oxide was reacted as described in Example 1, giving 1.2 g of the desired product, mp 250°–255° C. (dec.).

EXAMPLE 7

N-[3-(1H-Imidazol-1-yl)-1-phenylpropyl]benz[cd]indol-2-amine, fumarate

A mixture of 4 g of phenyl-3-(1H-imidazol-1-yl)propanamine, 3.7 g of benz[cd]indole-2-thiol, 250 ml of ethanol and 6 g of mercuric oxide was reacted as described in Example 1, giving the dihydrochloride salt of the desired product, which was then converted to the fumarate salt giving 0.7 g of the desired product, mp 125°–127° C.

EXAMPLE 8

N-[3-(1H-Imidazol-1yl)-2-methylpropyl]benz[cd]indol-2-amine, fumarate

A portion of the corresponding dihydrochloride salt, prepared in Example 6, was reacted as described in Example 4, giving 0.7 g of the fumarate salt, mp 150°–154° C.

EXAMPLE 9

N-[5-(1H-Imidazol-1-yl)pentyl]benz[cd]indol-2-amine, fumarate

A mixture of 1.55 g of 5-(1H-imidazol-1-yl)pentanamine, 3.3 g of 2-(methylthio)benz[cd]indole hydroiodide, and 200 ml of ethanol was reacted as described in Example 3, giving 4.6 g of the corresponding dihydrochloride salt, which was further reacted as described in Example 4, giving 1.6 g of the dedsired product, mp 159°–161° C. (dec.).

EXAMPLE 10

(Z)-N-[4-(1H-Imidazol-1-yl)-2-butenyl]benz[cd]indol-2-amine, dihydrochloride

A mixture of 2.5 g of (Z)-(1H-imidazol-1-yl)-2-butenamine, 5.9 g of 2-(methylthio)benz[cd]indole hydroiodide, and 500 ml of ethanol was reacted as described in Example 3, giving 0.7 g of the desired product, mp 215°–220° C. (dec.).

EXAMPLE 11

N-[3-(1H-Imidazol-1-yl)-2,2-diphenyl]benz[cd]indol-2-amine

A mixture of 3.3 g of 2-(methylthio)benz[cd]indole hydroiodide, 1.8 g of 1H-imidazole-1-(2,2-diphenyl)propanamine, 200 ml of ethanol and 0.9 g of sodium acetate was stirred at reflux for 18 hours, then diluted with 150 ml of water containing 1 g of sodium bicarbonate. This mixture was concentrated to turbidity and cooled at −10° C. The mixture was divided into two portions and each was extracted with two 200 ml portions of dichloromethane. All four extracts were combined, washed with 250 ml of water, dried over magnesium sulfate and filtered. The filtrate was evaporated at 40° C. The residual oil was extracted with two 100 ml portions of boiling hexane. The hexane was decanted, the residual solid washed with hexane, air dried and recrystallized from 200 ml of ethyl acetate, giving 1.3 g of the desired product, mp 229°–230° C.

EXAMPLE 12

(Z)-N-[4-(1H-Imidazol-1-yl)-2-butenyl]benz[cd]indol-2-amine and the corresponding fumarate salt A mixture of 3.3 g of 2-(methylthio)benz[cd]indole hydroiodide, 2.2 g of (Z)-4-(1H-imidazol-1-yl)-2-butenamine, 200 ml of ethanol and 0.9 g of sodium acetate was reacted as described in Example 11, giving the desired base which was then converted to the corresponding fumarate salt as described in Example 4, giving 1.8 g of the desired fumarate product, mp 85°–90° C.

EXAMPLE 13

N-[3-(2-Phenyl-1H-imidazol-1-yl)propyl]benz[cd]indol-2-amine, monohydroiodide

A mixture of 4.0 g of 3-(2-phenyl-1H-imidazol-1-yl)propanamine, 6.5 g of 2-(methylthio)benz[cd]indole hydroiodide, 1.8 g of sodium acetate and 250 ml of ethanol was reacted as described in Example 11. The crude product was recrystallized from a mixture of ethanol and isopropanol giving 3.8 g of the desired product, mp 153° C.–155° C.

EXAMPLE 14

N-[3-(2-Methyl-1H-imidazol-1-yl)propyl]benz[cd]indol-2-amine, monohydroiodide

A mixture of 2.1 g of 3-(2-methyl-1H-imidazol-1-yl)propanamine, 5.0 g of 2-(methylthio)benz[cd]indole hydroiodide, 1.4 g of sodium acetate and 250 ml of ethanol was reacted as described in Example 13, giving 1.0 g of the desired product, mp 153°–155° C.

EXAMPLE 15

N-[4-(1H-Imidazol-1-yl)butyl]benz[cd]indol-2-amine, monohydroiodide

A 2.2 g portion 4(1H-imidazol-1-yl)butanamine dihydrochloride and 2 ml of 10N sodium hydroxide in 200 ml of ethanol was stirred for 10 minutes and then treated with 3.2 g of 2-(methylthio)benz[cd]indole hydroiodide. This mixture was heated at reflux for 16 hours and then cooled to −10° C. The mixture was reheated to boiling, clarified while hot and the filtrate cooled to −10° C. The solid was collected, washed with ethanol, then ether and dried at 60° C. in vacuo, giving 2.0 g of the desired product, mp 144°–147° C.

EXAMPLE 16

(E)-N-[4-(1H-Imidazol-1-yl)-2-butenyl]benz[cd]indol-2-amine, monohydroiodide

A mixture of 5.0 g of (E)-4-(1H-imidazol-1-yl)-2-butenamine, 11.5 g of 2-(methylthio)benz[cd]indole hydroiodide and 400 ml of ethanol was stirred and heated at reflux for 16 hours, then clarified while hot. The filtrate was concentrated to 250 ml, cooled to −10° C. and the resulting solid collected, washed with ethanol, ether and dried at 60° C. in vacuo, giving 9.3 g of the desired product, mp 152°–155° C. (dec.).

EXAMPLE 17

N-[3-(1H-Benzimidazol-1-yl)propyl]benz[cd]indol-2-amine and fumarate salt

A mixture of 2.6 g of 3-(1H-benzimidazol-1-yl)propanamine, 2.8 g of benz[cd]-indole-2-thiol, 3.8 g of mercuric oxide and 250 ml of ethanol was reacted as described in Example 1, giving 1.5 g of the desired base mp 191°–193° C., which was then converted to the fumarate salt as described in Example 4, giving 1.3 g of the desired product as the fumarate salt, mp 155°–158° C.

EXAMPLE 18

N-[4-(1H-Imidazol-1-yl)butyl]benz[cd]indol-2-amine, fumarate

A 2.2 g portion of 4-(1H-imidazol-1-yl)butanamine dihydrochloride and 2 ml of 10N sodium hydroxide in 200 ml of ethanol was stirred for 10 minutes and then treated with 3.2 g of 2-(methylthio)benz[cd]indole hydroiodide. This mixture was heated at refluxed for 16 hours, and then taken to dryness in vacuo. The residue was partitioned between 250 ml of dichloromethane and 100 ml of 1N sodium hydroxide. The dichloromethane layer was dried over magnesium sulfate, filtered and the filtrate evaporated giving the crude base derivative. This base was treated with 1.5 g of fumaric acid in 400 ml of acetone, giving 2.4 g of the desired product, mp 153°–155° C. (dec.).

EXAMPLE 19

N-[5-(1-Imidazol-1-yl)-3-methylpentyl]benz[cd]indol-2-amine, dihydrochloride

A 2.9 g portion of 5-(1H-imidazol-1-yl)-3-methylpentanamine in 350 ml of ethanol was treated with 5.5 g of 2-(methylthio)benz[cd]indole hydroiodide and stirred at reflux for 18 hours. The mixture was concentrated to 175 ml, cooled to −10° C. and clarified. The filtrate was taken to dryness in vacuo and the residue partitioned between 250 ml of dichloromethane and 100 ml 1N sodium hydroxide. The dichloromethane layer was dried over magnesium sulfate, clarified and evaporated to dryness. The residue was dissolved in 400 ml of acetone, treated with 10 ml of 3.5N hydrochloric acid in ethanol, then concentrated to 200 ml on a stream bath and diluted to turbidity with ether. The mixture was cooled to −10° C. and the solid collected, washed with acetone and dried in vacuo at 60° C., giving 1.5 g of the desired product, mp 113°–116° C. (dec.).

EXAMPLE 20

N-[10-(1H-Imidazol-1-yl)decyl]benz[cd]indol-2-amine, fumarate and dihydrochloride A mixture of 6.6 g of 10-(1H-imidazol-1-yl)decanamine, 500 ml of ethanol and 9.8 g of 2-(methylthio)benz[cd]indole hydroiodide was reacted as described in Example 19, giving 9.7 g of the base form of the desired compound as a brown oil. A portion of this base was converted to the desired fumarate salt by the procedure described in Example 4, giving 1.1 g, mp 135°–136° C.

A portion of the base derivative was converted to the dihydrochloride salt by treatment with hydrochloric acid in ethanol, giving 3.5 g mp 103°–105° C.

EXAMPLE 21

N-[2-(1H-Imidazol-1-yl)ethyl]benz[cd]indol-2-amine, base and fumarate salt

A mixture 1.25 g of 2-(1H-imidazol-1-yl)ethanamine, 300 ml of ethanol and 2.5 g of 2-(methylthio)benz[cd]indole, hydrochloride was reacted as described in Example 19, giving 1.4 g of the base derivative, mp 172°–173° C.

A portion of this base was then converted to the fumarate salt as described in Example 4, giving 1.0 g, mp 210°–212° C. (dec.).

EXAMPLE 22

N-[2-[2-(1H-Imidazol-1-yl)ethoxy]ethyl]benz[cd]indol-2-amine, fumarate

A mixture of 1.7 g of 2-[2-(1H-imidazol-1-yl)ethoxyethanamine], 600 ml of ethanol, and 3.2 g of 2-(methylthio)benz[cd]indole, hydroiodide was reacted as described in Example 19, giving the base derivative which was then converted to the fumarate salt by the procedure of Example 4, giving 2.1 g, mp 153°–154° C. (dec.).

EXAMPLE 23

N-[8-(1H-Imidazol-1yl)octyl]benz[cd]indole-2-amine, dihydrochloride

A mixture of 2.1 g of 8-(1H-imidazol-1-yl)octanamine, 400 ml of ethanol, and 3.2 g of 2-(methylthio)-benz[cd]indole hydroiodide was reacted as described in Example 19, giving the base derivative which was then treated with hydrochloric acid giving 1.3 g of the desired hydrochloride salt, mp 222°–224° C.

EXAMPLE 24

2-(Benz[cd]indole-2-ylamino)-N-[3-(1H-imidazol-1yl)-propyl]acetamide

A mixture of 3.7 g of N-[3-(1H-imidazol-1-yl)propyl]-glycinamide, 425 ml of ethanol, and 5.0 g of 2-(methylthio)benz[cd]indole hydroiodide was reacted as described in Example 19, giving 2.2 g of the desired product, mp 145°–146° C.

EXAMPLE 25

N-[[4-(1H-Imidazol-1-ylmethyl)phenyl]methyl]benz[cd]indol-2-amine, fumarate

A mixture of 2.8 g of 4-(1H-imidazol-1-yl)methylbenzylamine, 250 ml of ethanol and 4.7 g of 2-(methylthio)-benz[cd]indole hydroiodide was reacted as described in Example 19 giving the base derivative which was then reacted as described in Example 4, giving 6.6 g of the fumarate salt, mp 200°–205° C.

EXAMPLE 26

N-[4-(1H-Imidazol-1-yl)pentyl]benz[cd]-2-amine, fumarate

A mixture of 2.8 g of 4-(1H-imidazol-1-yl)pentanamine 3.3 g of benz[cd]indole-2-thiol, 7.0 g of mercuric acetate and 500 ml of ethanol was reacted as described in Example 1, giving the base derivative which was converted to the fumarate salt as described in Example 4, giving 5.6 g, mp 173°–175° C.

EXAMPLE 27

6-Bromo-N-[3-(1H-imidazol-1-yl)butyl]benz[cd]indol-2-amine

A mixture of 5.2 g of 6-bromo-benz[cd]indole-2-thiol, 2.8 g of 3-(1H-imidazol-1-yl)butanamine, 6.6 g of mercuric acetate and 100 ml of dry p-dioxane was reacted as described in Example 1, giving 3.0 g of the desired product, mp 240°–241° C.

EXAMPLE 28

2-[[3-(1H-Imidazol-1-yl)butyl]amino]-N,N-dimethyl-benz[cd]indol-6-sulfonamide

A mixture of 7.3 g of 1,2-dihydro-N,N-dimethyl-2-thioxobenz[cd]indole-6-sulfonamide, 4.2 g of 3-(1H-imidazol-1-yl-butanamine, 150 ml of ethanol and 9.6 g of mercuric acetate was reacted as described in Example 1, giving 5.5 g of the desired product, mp 221°–222° C.

EXAMPLE 29

2-[[3-(1H-Imidazol-1-yl)propyl]amino]-N,N-dimethyl-benz[cd]indol-6-sulfonamide

A mixture 5 g of 1,2-dihydro-N,N-dimethyl-2-thioxobenz[cd]indole-6-sulfonamide, 2.3 g of 3-(1H-imidazol-1-yl)propanamine, 100 ml of ethanol and 5.4 g of mercuric acetate was reacted as described in Example 1, giving 2.7 g of the desired product, mp 199°–201° C.

EXAMPLE 30

6-Bromo-N-[10-(1H-imidazol-1-yl)decyl]benz[cd]indol-2-amine

A mixture of 2.8 g of 10-(1H-imidazol-1-yl)decanamine, dihydrochloride was treated with 2 ml of 10N sodium hydroxide in an ethanol-water mixture giving the base derivative. To this base was added 25 ml of ethanol, 2.33 g of 6-bromo-benz[cd]indole-2-thiol and 3 g of mercuric acetate. The procedure of Example 1 was then followed, giving 2.8 g of the desired product, mp 115°–116° C.

EXAMPLE 31

6-Bromo-N-[4-(1H-imidazol-1-yl)butyl]benz[cd]indol-2-amine

A mixture 4.2 g of 4-(1H-imidazol-1-yl)butanamine dihydrochloride in 75 ml of ethanol was treated with 2.2 g of potassium hydroxide and stirred for 18 hours. A 5.2 g portion of 6-bromo-benz[cd]indole-2-thiol and 6.4 g of mercuric acetate were added and the reaction proceeded as described in Example 1, giving 3.7 g of the desired product, mp 145°–147° C.

EXAMPLE 32

6,8-Dichloro-N-[10-(1H-imidazol-1-yl)decyl]-benz[cd]indol-2-amine

A 2.8 g portion of 10-(1H-imidazol-1-yl)decanamine, dihydrochloride in an ethanol-water mixture was treated with 2 ml of 10N sodium hydroxide, stirred and evaporated to dryness. To the residue was added 35 ml of dry dimethylformamide, 3 g of mercuric acetate and 2.2 g of 6,8-dichloro-benz[cd]indole-2-thiol. The reaction proceeded as described in Example 1, giving 2.3 g of the desired product, mp 129°–131° C.

EXAMPLE 33

6,8-Dichloro-N-[3-(1H-imidazol-1-yl)butyl]benz[cd]indol-2-amine

A mixture of 7.0 g of 6,8-dichloro-benz[cd]indole-2-thiol, 100 ml of ethanol, 9.5 g of mercuric acetate and 4.2 g of 4-(1H-imidazol-1-yl)-2-butanamine was reacted as described in Example 1, giving 1.7 g of the desired product, mp 244°–246° C. (dec.).

EXAMPLE 34

6,8-Dichloro-N-[3-(1H-imidazol-1-yl)propyl]benz[cd]indol-2-amine

A mixture of 5.0 g of 6,8-dichloro-benz[cd]indole-2-thiol, 35 ml of dimethylformamide, 2.6 g of 3-(1H-imidazol-yl)propanamine and 6.3 g of mercuric acetate was reacted as described in Example 1, giving 2.95 g of the desired product, mp 182°–183° C.

EXAMPLE 35

6,8-Dichloro-N-[4-(1H-imidazol-1-yl)butyl]benz[cd]indol-2-amine

A 4.2 g portion of 4-(1H-imidazol-1-yl)butanamine, dihydrochloride was suspended in 75 ml of ethanol, treated with 2.24 g of potassium hydroxide, stirred for 6 hours and evaporated. A 35 ml portion of dimethylformamide, 5.0 g of 6,8-dichloro-benz[cd]indole-2-thiol and 6.3 g of mercuric acetate were added and the reaction proceeded as described in Example 1, giving 2.5 g of the desired product, mp 187°–188° C.

EXAMPLE 36

6-Bromo-N-[5-(1H-imidazol-1-yl)pentyl]benz[cd]indol-2-amine

A mixture of 5.3 g of 6-bromo-benz[cd]indole-2-thiol, 3.1 g of 5-(1H-imidazol-1-yl)pentanamine, 100 ml of ethanol and 6.3 g of mercuric acetate was reacted as described in Example 1, giving 1.5 g of the desired product, mp 138°–140° C.

EXAMPLE 37

6,8-Dichloro-N-[5-(1H-imidazol-1-yl)pentyl]benz[cd]indol-2-amine

A mixture of 5.0 g of 6,8-dichloro-benz[cd]indole-2-thiol, 3.1 g of 5-(1H-imidazol-1-yl)pentanamine, 100 ml of dry dimethylformamide and 6.3 g of mercuric acetate was reacted as described in Example 1, giving 1.8 g of the desired product, mp 191°–192.5° C.

EXAMPLE 38

N-[12-(1H-Imidazol-1-yl)dodecyl]benz[cd]indol-2-amine

A mixture of 2.5 g of 12-(1H-imidazol-1-yl)dodecanamine, 1.9 g of benz[cd]indole-2-thiol, 3.4 g of mercuric acetate and 400 ml of ethanol was reacted as described in Example 1. The crude product was purified by dissolving it in chloroform and chromatographing it on a silica gel column, eluting with 10% methanol in chloroform giving 490 mg of the desired product, mp 95°–97° C.

EXAMPLE 39

6-Bromo-N-[12-(1H-imidazol-1-yl)dodecyl]benz[cd]indol-2-amine

The procedure of Example 38 was repeated using 2.65 g of 6-bromo-benz[cd]indole-2-thiol instead of 1.9 g of benz[cd]indole-2-thiol, giving 720 mg of the desired product, mg 111°–116° C.

EXAMPLE 40

6-Chloro-N-[5-(1H-imidazol-1-yl)pentyl]benz[cd]indol-2-amine

A mixture of 4.4 g of 6-chloro-benz[cd]indole-2-thiol, 3.06 g of 5-(1H-imidazol-1-yl)pentanamine, 6.3 g of mercuric acetate and 150 ml of ethanol was reacted as described in Example 1, giving 5.2 g of the desired product, mp 132°–134° C.

EXAMPLE 41

6-Chloro-N-[4-(1H-imidazol-1-yl)butyl]benz[cd]indol-2-amine, fumarate

A mixture of 4.4 g of 6-chloro-benz[cd]indole-2-thiol, 2.8 g of 4-(1H-imidazol-1-yl)butanamine, 6.3 g of mercuric acetate and 150 ml of ethanol was reacted as described in Example 1, giving the free base form. This free base was converted to the fumarate salt by the procedure of Example 4, giving 4.8 g mp 190°–192° C.

EXAMPLE 42

6-Chloro-N-[3-(1H-imidazol-1-yl)propyl]benz[cd]indol-2-amine

A mixture of 1 g of 6-chloro-benz[cd]indole-2-thiol, 540 mg of 3-(1H-imidazol-1-yl)propanamine, 1.26 g of mercuric acetate and 100 ml of ethanol was reacted as described in Example 1, giving 1 g of the desired compound, mp 177°–178° C.

EXAMPLE 43

N-[3-(1H-Imidazol-1-yl)propyl]benz[cd]indol-2-amine, difumarate

The free base, N-[3-(1H-imidazol-1-yl)propyl]benz[cd]indol-2-amine (prepared as described in Example 1) was dissolved in 20 parts (by weight) of acetone and this solution added dropwise to a vigorously stirred, refluxing solution of 2.2 equivalents of fumaric acid in 150 parts of acetone. After cooling to room temperature, the bright yellow precipitate was collected, washed with acetone and dried in vacuo at 60° C., giving the desired fumarate salt, mp 165°–166° C. (dec.). (Reference: CL 295,446, NB 12749B-86, 89)

What is claimed is:

1. A compound of the formula:

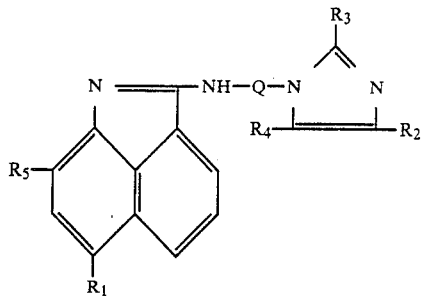

wherein $R_1$ is hydrogen, bromo, chloro or dimethylaminosulfonamide; $R_2$ is hydrogen or alkyl($C_1$–$C_3$); $R_3$ is hydrogen, alkyl($C_1$–$C_3$) or phenyl; $R_4$ is hydrogen or when taken together with $R_2$ is —CH=CH—CH=CH—; $R_5$ is hydrogen or chloro; and Q is —(CH$_2$)$_n$—, where n is an integer 2–12,

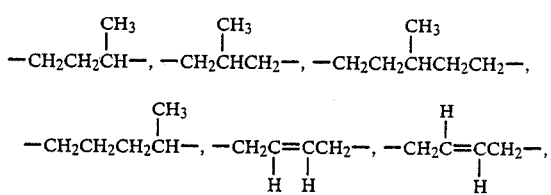

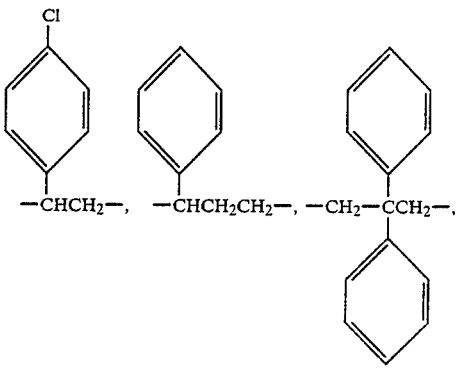

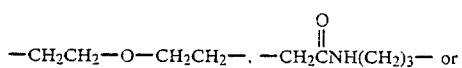

and the pharmacologically acceptable salts thereof.

2. The compound according to claim 1, N-[4-(1H-imidazol-1-yl)butyl]benz[cd]indol-2-amine.

3. The compound according to claim 1, N-[3-(1H-imidazol-1-yl)propyl]benz[cd]indol-2-amine.

4. The compound according to claim 1, 6-bromo-N-[3-(1H-imidazol-1-yl)butyl]benz[cd]indol-2-amine.

5. The compound according to claim 1, 6-bromo-N-[5-(1H-imidazol-1-yl)pentyl]benz[cd]indol-2-amine.

6. The compound according to claim 1, 6,8-dichloro-N-[5-(1H-imidazol-1-yl)pentyl]benz[cd]indol-2-amine.

7. The compound according to claim 1, 6-chloro-N-[4-(1H-imidazol-1-yl)butyl]benz[cd]indol-2-amine.

8. The compound according to claim 1, N-[3-(1H-imidazol-1-yl)-1-phenylpropyl]benz[cd]indol-2-amine.

9. The compound according to claim 1, N-[3-(1H-imidazol-1-yl)-2-methylpropyl]benz[cd]indol-2-amine.

10. The compound according to claim 1 (E)-N-[4-(1H-imidazol-1-yl)-2-butenyl]benz[cd]indol-2-amine.

11. The compound according to claim 1, 2-[[3-(1H-imidazol-1-yl)butyl]amino]-N,N-dimethylbenz[cd]indol-6-sulfonamide.

12. The compound according to claim 1, 2-[[3-(1H-imidazol-1-yl)propyl]amino]-N,N-dimethylbenz[cd]indol-6-sulfonamide.

13. The compound according to claim 1, 2-(benz[cd]indole-2-ylamino)-N-[3-(1H-imidazol-1-yl)propyl]acetamide.

14. The compound according to claim 1, (Z)-N-[4-(1H-imidazol-1-yl)-2-butenyl]benz[cd]indol-2-amine.

15. The compound according to claim 1, N-[5-(1H-imidazol-1-yl)-3-methylpentyl]benz[cd]indol-2-amine.

16. The compound according to claim 1 6,8-dichloro-N-[3-(1H-imidazol-1-yl)propyl]benz[cd]indol-2-amine.

17. The method of inhibiting thromboxane synthetase enzyme in a mammal which comprises administering internally to said mammal a thromboxane synthetase enzyme inhibiting amount of a compound of claim 1.

18. A thromboxane synthetase enzyme inhibiting composition of matter in dosage unit form comprising from about 10 mg to about 700 mg of a compound of claim 1 in association with a pharmacologically acceptable carrier.

19. A method of inhibiting hypertension in a mammal which comprises administering to said mammal a hypotensive amount of a compound of claim 1.

20. A method of inhibiting arrhythmia in a mammal which comprises administering internally to said mammal an arrhythmia inhibiting amount of a compound of claim 1.

21. A method for blocking α-adrenoceptors on heart muscle in a mammal which comprises administering internally to mammal a α-adrenoceptor blocking amount of a compound of claim 1.

22. A process for producing a compound of the formula:

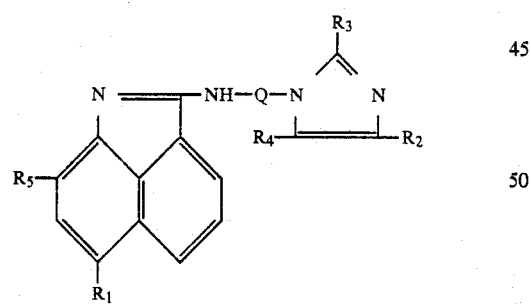

wherein $R_1$ is hydrogen, bromo, chloro or dimethylaminosulfonamide; $R_2$ is of hydrogen, or alkyl($C_1$-$C_3$), $R_3$ is hydrogen, alkyl($C_1$-$C_3$), or phenyl; $R_4$ is hydrogen or when taken together with $R_2$ is —CH=CH—CH=CH; $R_5$ is hydrogen or chloro; and Q is —(CH$_2$)$_n$—, where n is an integer 2–12,

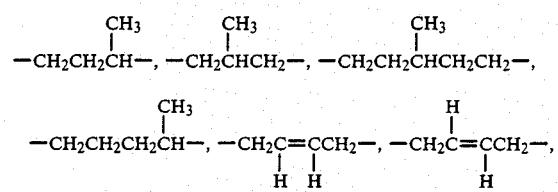

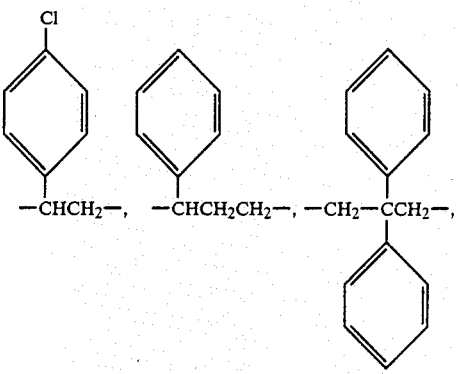

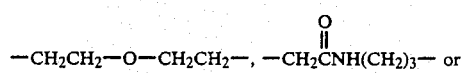

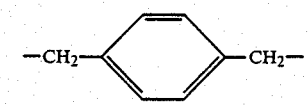

and the pharmacologically acceptable salts which comprises reacting a substituted 2-methylthiobenz[cd]indole salt of the structure

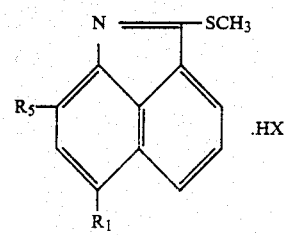

where X is halogen, methylsulfate, sulfate, or the like with a substituted (1H-imidazol-1-yl)alkanamine of the formula

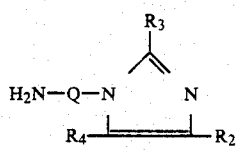

in a solvent such as ethanol at reflux temperature for 6–24 hours.

23. The compound according to claim 1, N[4-(1H-imidazol-1-yl)butyl]benz[cd]indol-2-amine, fumarate.

* * * * *